United States Statutory Invention Registration [19]

[11] Reg. Number: H306

Ducote et al. [43] Published: Jul. 7, 1987

[54] METHOD FOR PREPARATION OF AMINE SALT BONDING AGENTS

[75] Inventors: Marjorie E. Ducote; James G. Carver, both of Huntsville, Ala.

[73] Assignee: The United States of America as represented by the Secretary of the Army, Washington, D.C.

[21] Appl. No.: 874,312

[22] Filed: Jun. 9, 1986

[51] Int. Cl.[4] ..... C07C 121/42; C07C 121/453

[52] U.S. Cl. ..... 558/452; 558/451

[56] References Cited

U.S. PATENT DOCUMENTS 4,493,741 1/1985 Ducote et al. ..... 149/19.4

*Primary Examiner*—John F. Terapane
*Assistant Examiner*—Susan Wolffe
*Attorney, Agent, or Firm*—John C. Garvin, Jr.; Freddie M. Bush; Anthony Thomas Lane

[57] ABSTRACT

A stoichiometric amount of a polyamine compound selected from the group consisting of cyanoethyl substituted tetraethylene pentamine (TEPAN), or the glycidol reaction product of cyanoethyl substituted tetraethylene pentamine (TEPANOL) is reacted with a stoichiometric amount of perchloric acid to yield an amine salt bonding agent useful in propellant compositions.

This improved method prevents the generation of ammonia (as in prior art method) which has to be removed prior to use of amine salt bonding agent in a propellant composition. Also, a lesser amount of diluent water is involved in this method which offers an advantage by not having to strip an excessive amount of water by heat, purge, or vacuum means.

The amine salt bonding agents prepared by this improved method are shown to be of like identity and quality as shown by IR spectroscopic examination and their testing in a propellant composition.

2 Claims, 2 Drawing Figures

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR PREPARATION OF AMINE SALT BONDING AGENTS

DEDICATORY CLAUSE

The invention described herein may be manufactured, used, and licensed by or for the Government for governmental purposes without the payment to us of any royalties thereon.

BACKGROUND OF THE INVENTION

Certain amine compounds such as TEPAN, a partially cyanoethylated tetraethylene pentamine, have long been used in the propellant industry as bonding agents in composite propellants containing ammonium perchlorate (AP). They greatly improve the mechanical properties of such propellants by chemically bonding AP particles to the binder matrix. TEPAN is also known to facilitate processing relative to other bonding agents since the mix viscosity of the propellant is not increased as much by TEPAN as it is by most other bonding agents. The disadvantage of using amine bonding agents is that ammonia is liberated during the mix and cure cycles due to displacement of ammonia from AP by amine groups in the bonding agent. The amine-ammonium perchlorate reaction requires subsequent ammonia removal from the mix because any residual ammonia will consume part of the isocyanate curing agent and thus interfere with propellant cure.

In a prior, commonly assigned U.S. Pat. No. 4,493,741 entitled "Amine Salts as Bonding Agents", ammonium salt adducts of TEPAN and TEPANOL and their processes for preparation are disclosed. The process for preparation of the adduct of TEPAN comprises reacting a water solution of the selected ammonium salt with TEPAN while stirring at room temperature. Similarly, a TEPAN-glycidol derivative product (TEPANOL) is also reacted with an ammonium salt to form the adduct of TEPANOL. The ammonium salt is selected from ammonium perchlorate (AP), ammonium nitrate (AN), ammonium sulfate (AS), and ammonium formate (AF).

Mechanical properties of a propellant composition, especially strain at maximum stress at −40° C. are substantially improved. The processing time, particularly the mix cycle time is shortened because of the amine salt bonding agent eliminating or minimizing in situ ammonia generation during the incorporation and mixing of ammonium perchlorate into the propellant mix.

As noted in the above described procedure from the prior U.S. Pat. No. 4,493,741 preparation of the amine salts involved solvation of the ammonium salt such as ammonium perchlorate, ammonium sulfate, etc. in distilled water, addition to the polyamine with stirring, and digestion for several hours at 170° C. or above. After these preparatory steps, ammonia and the copious amount of water present had to be stripped off by heat, purge, and vacuum.

An advantage of a more concise method of preparation of adducts of TEPAN and TEPANOL, provided the end products are comparable in quality, is readily recognized.

Therefore an object of this invention is to provide a method for changing the polyamine to the corresponding ammonium salt that reduces the amount of water to be removed from the finished product by a substantial amount.

A further object of this invention is to provide a method which employs the appropriate mineral acid for reacting directly with TEPAN or TEPANOL to yield the corresponding ammonium salt adduct without generation of noxious ammonia fumes.

SUMMARY OF THE INVENTION

The method of this invention comprises reacting a polyamine compound selected from the group consisting of cyanoethyl substituted tetraethylene pentamine, and the glycidol reaction product of cyanoethyl substituted tetraethylene pentamine with a stoichiometric ratio of perchloric acid by slowly adding with stirring the specified ratio of a 60% to 70% perchloric acid solution to the polyamine compound for approximately 10 minutes to obtain homogeneity, and thereafter, transferring the mixed reaction mixture to a vessel and stripping the diluent water from the reaction product.

DESCRIPTION OF THE PREFERRED EMBODIMENTS

A polyamine compound selected from the group consisting of cyanoethyl substituted tetraethylene pentamine (TEPAN), and the glycidol reaction product of cyanoethyl substituted tetraethylene pentamine (TEPANOL) is reacted with a stoichiometric ratio of perchloric acid to yield an adduct reaction product having only diluent water from perchloric acid solution that is subsequently stripped from the adduct reaction product.

The method reaction using TEPAN and perchloric acid as the reactants is as set forth under Example I below.

EXAMPLE I

| Reactant | Weight of Reactant (grams) |
|---|---|
| (1) TEPAN | 25.2 grams |
| (2) Perchloric acid* | 21.3 grams |

*60% perchloric acid.

Note:

70% perchloric acid reduces water to less than 3% as compared to less than 18% water when 60% perchloric acid is reactant (2).

DIRECTIONS

TEPAN, 25.2 grams, is weighed and placed in a glass beaker. Perchloric acid (60%) in an amount of about 21.3 grams is slowly added with stirring to the TEPAN. After mixing for approximately 10 minutes to achieve homogeneity the reactant mixture is transferred to a vessel appropriate for stripping the less than 18% residual or diluent water from the product. In the prior art process, product at this point would be diluted by at least half with water.

IR spectroscopic examination of the above reaction product prepared by this method is the same as that prepared by the old procedure. Compare IR curves, FIGS. 1 and 2. However, the prior method required ammonia and the copious amount of water present to be stripped off by heat, purge, and vacuum. The prior art method involves several additional steps and requires much greater preparation time than the method of this invention.

Figure 1:
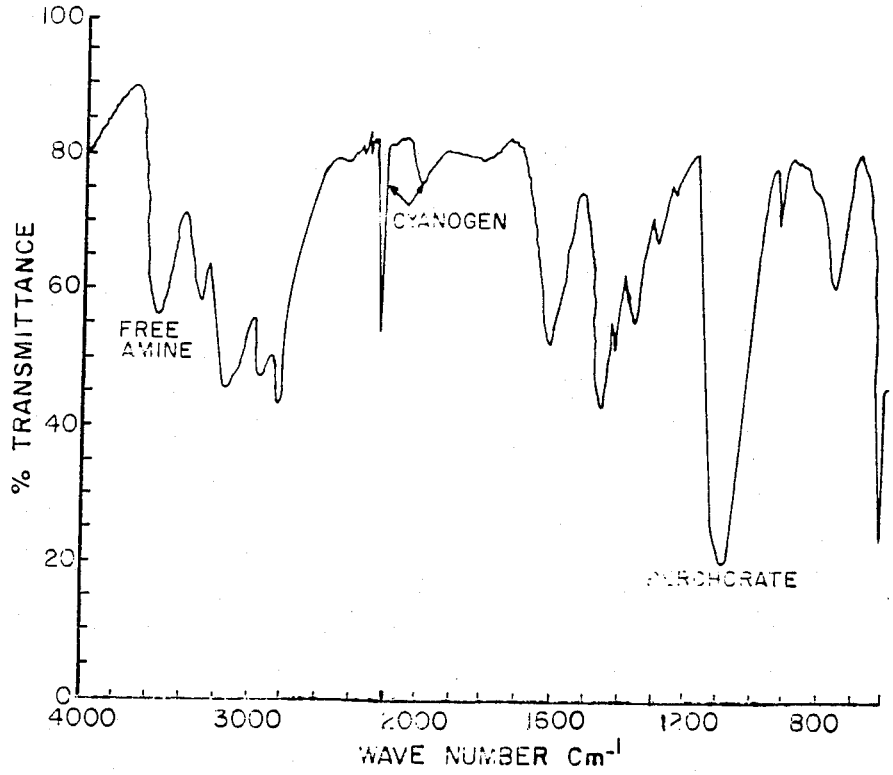
FIG. 1 PRIOR ART
FIG. 1 of the drawing is an IR spectrograph depicting % transmittance versus wave number $cm^{-1}$ of the adduct of cyanoethyl substituted tetraethylene pentamine and ammonium perchlorate prepared by a prior art method; and, FIG. 2 of the drawing is an IR spectrograph depicting % transmittance versus wave number $cm^{-1}$ of the adduct reaction product of cyanoethyl substituted tetraethylene pentamine and perchloric acid prepared by the method of this invention.
Figure 2:
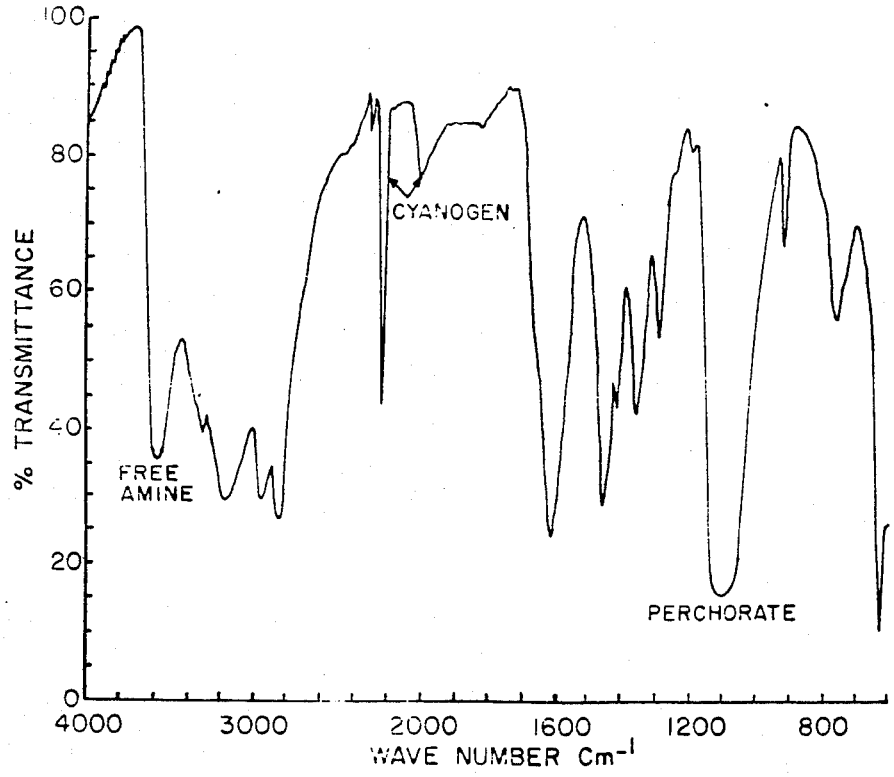

The disclosed method is applicable to preparation of all amine salt bonding agents described in U.S. Pat. No. 4,493,741 by substituting the corresponding stoichiometric ratio of reactants. Since the finished bonding agent shown by IR spectroscopic examination, as depicted by FIGS. 1 and 2, to be equivalent identites for its intended use, the advantages set forth hereinabove for improved method are readily recognized. Also, the use of this amine bonding agent in a baseline propellant is shown under Example II below. This combination further illustrates the proven performance of an identical amine bonding agent made by the new method of this invention.

EXAMPLE II

| BASELINE PROPELLANT COMPOSITION | |
|---|---|
| R45HT - IPDI (56 parts) | 9.81-9.61 |
| DOA Dioctyl adipate | 2% |
| Bonding agent* | 0.15-0.35 |
| Al | 18% |
| AP 200/17 | 69% |
| $Fe_2O_3$ | 1% |
| TPB, (Triphenyl bismuth) | 0.02% |
| MA (Maleic anhydride) | 0.02% |

*Reaction adduct product of TEPAN/or TEPANOL and perchloric acid.

An experimental propellant formulation set forth under Example III, below, further compares physical properties of the propellant using TC-18 prepared by prior art process and the new process of this invention, TC-16 new process of this invention, and the parent compound TEPAN. The term TC-18 and TC-16 for identifying the amine salt bonding agent includes the amine TEPAN with about 1.8 and 1.6 equivalent ammonium ion donor per mole of polyamine. In each example there would be a nominal unreacted amine equivalents of about 3.2 and about 3.4 respectively for the TC-18 and TC-16 since prior to reacting there are about five amine equivalents present as secondary and a few tertiary amines (confirmed by IR). For further information and comparison of propellant properties employing the amine salt bonding agents see Example III below and related comments.

EXAMPLE III

| EXPERIMENTAL PROPELLANT FORMULATION | |
|---|---|
| Ingredient | Weight Percent |
| R45HT/IPDI hydroxyterminated polybutadiene/isophorone diisocyanate (Binder and Crosslinking Agent) | 9.75 |
| Plasticizer | 2.00 |
| TC-18 | 0.25 |
| $Fe_2O_3$ | 1.00 |
| Al | 17.00 |
| AP | 70.00 |

Propellant Formulation Physical Properties Values

| Amine Salt Bonding Agent | Stress (psi) | Strain at (%) Max/Stress/ Break | Modulus (Psi) |
|---|---|---|---|
| TC-18 Prepared by prior art process Tested at: | | | |
| +140° F. | 69 | 25/27 | 409 |
| 70 | 104 | 32/34 | 696 |
| −40 | 291 | 39/43 | 5928 |
| TC-18 prepared by new process Tested at: | | | |
| +140° F. | 82 | 34/34 | 412 |
| 70° | 99 | 37/37 | 563 |
| −40° | 311 | 40/43 | 3202 |
| TC-16 prepared by new process Tested at: | | | |
| +140° F. | 77 | 26/28 | 442 |
| 70° | 97 | 29/29 | 584 |
| −40° | 338 | 35/36 | 3117 |
| Parent Compound TEPAN Tested at: | | | |
| +140 | 79 | 23/23 | 514 |
| 70° | 95 | 26/26 | 596 |
| −40° | 327 | 29/30 | 5260 |

The above data verifies the quality of the amine salt bonding agent by its function in a propellant composition.

We claim:

1. A method for preparing an amine salt bonding agent comprising:
   (i) adding a predetermined stoichiometric amount of a polyamine compound selected from a cyanoethyl substituted tetraethylene pentamine and the glycidol reaction product of cyanoethyl substituted tetraethylene pentamine to a reaction container;
   (ii) slowly adding with stirring a predetermined amount of a stoichiometric amount of perchloric acid to said polyamine compound, and continue stirring to achieve a homogenious mixture;
   (iii) transferring said homogenous mixture to a vessel appropriate for stripping diluent water; and,
   (iv) stripping diluent water from said reaction mixture and recovering said amine salt bonding agent.

2. The method of claim 1 wherein said polyamine compound selected is cyanoethyl substituted tetraethylene pentamine, said stoichiometric amount of said polyamine compound is about 25.2 grams, said stoichiometric amount of said perchloric acid which is 60% perchloric is about 21.3 grams, and wherein about 18 percent diluent water is stripped from said homogenous mixture and said amine salt bonding agent is recovered.

* * * * *